United States Patent
Sournac et al.

(10) Patent No.: US 8,828,083 B2
(45) Date of Patent: Sep. 9, 2014

(54) INTERVERTEBRAL DISK PROSTHESIS NOTABLY FOR CERVICAL VERTEBRAE

(75) Inventors: Denys Marc Sournac, Reyrieux (FR); Thomas Mosnier, Anthon (FR); David N. Ryan, Collonges au Mont d'Or (FR)

(73) Assignee: Medicrea International, Neyron (FR)

( * ) Notice: Subject to any disclaimer, the term of this patent is extended or adjusted under 35 U.S.C. 154(b) by 444 days.

(21) Appl. No.: 12/922,234

(22) PCT Filed: Mar. 25, 2009

(86) PCT No.: PCT/IB2009/051236
§ 371 (c)(1),
(2), (4) Date: Oct. 28, 2011

(87) PCT Pub. No.: WO2009/118691
PCT Pub. Date: Oct. 1, 2009

(65) Prior Publication Data
US 2012/0116512 A1   May 10, 2012

(30) Foreign Application Priority Data
Mar. 25, 2008   (FR) .................... 08 01597

(51) Int. Cl.
A61F 2/44   (2006.01)
A61F 2/30   (2006.01)

(52) U.S. Cl.
CPC ..... *A61F 2/4425* (2013.01); *A61F 2002/30069* (2013.01); *A61F 2002/30331* (2013.01); *A61F 2002/443* (2013.01); *A61F 2220/0025* (2013.01); *A61F 2220/0033* (2013.01); *A61F 2002/30649* (2013.01); *A61F 2002/30369* (2013.01); *A61F 2002/305* (2013.01); *A61F 2310/00179* (2013.01); *A61F 2002/30604* (2013.01); *A61F 2002/30224* (2013.01); *A61F 2002/30904* (2013.01); *A61F 2230/0069* (2013.01); *A61F 2230/0065* (2013.01); *A61F 2002/302* (2013.01); *A61F 2002/30563* (2013.01); *A61F 2002/30894* (2013.01)
USPC ........................................... 623/17.16

(58) Field of Classification Search
USPC ............................ 623/17.11–17.16
See application file for complete search history.

(56) References Cited

U.S. PATENT DOCUMENTS

2003/0191534 A1* 10/2003 Viart et al. ................. 623/17.15
2004/0054411 A1   3/2004 Kelly et al.

(Continued)

FOREIGN PATENT DOCUMENTS

EP          1 532 950 A1   5/2005
WO    WO 2005/079407 A2   9/2005

OTHER PUBLICATIONS

Written Opinion of the International Searching Authority issued in corresponding International Application No. PCT/IB2009/051236, mailed Jul. 6, 2009.

(Continued)

*Primary Examiner* — Andrew Yang
*Assistant Examiner* — Diana S Jones
(74) *Attorney, Agent, or Firm* — Oliff PLC

(57) ABSTRACT

A prosthesis comprises having two portions independent of each other, a first portion and a second portion, at least one of which includes an articular surface, said first portion and said second portion each comprising a circular seat delimited by an arched wall. An element of the prosthesis is an O-ring in an elastically deformable material, and one of said seats is dimensioned to receive a radially outer portion of this ring while the other seat is dimensioned to receive a radially inner portion of this ring.

12 Claims, 5 Drawing Sheets

(56) References Cited

U.S. PATENT DOCUMENTS

| | | |
|---|---|---|
| 2005/0165485 A1 | 7/2005 | Trieu |
| 2005/0187632 A1* | 8/2005 | Zubok et al. ............... 623/17.14 |
| 2005/0251260 A1* | 11/2005 | Gerber et al. ............. 623/17.14 |
| 2005/0261772 A1 | 11/2005 | Filippi et al. |
| 2007/0185579 A1* | 8/2007 | Naegerl .................... 623/17.15 |

OTHER PUBLICATIONS

International Search Report issued in corresponding International Application No. PCT/IB2009/051236, mailed Jul. 6, 2009.

* cited by examiner

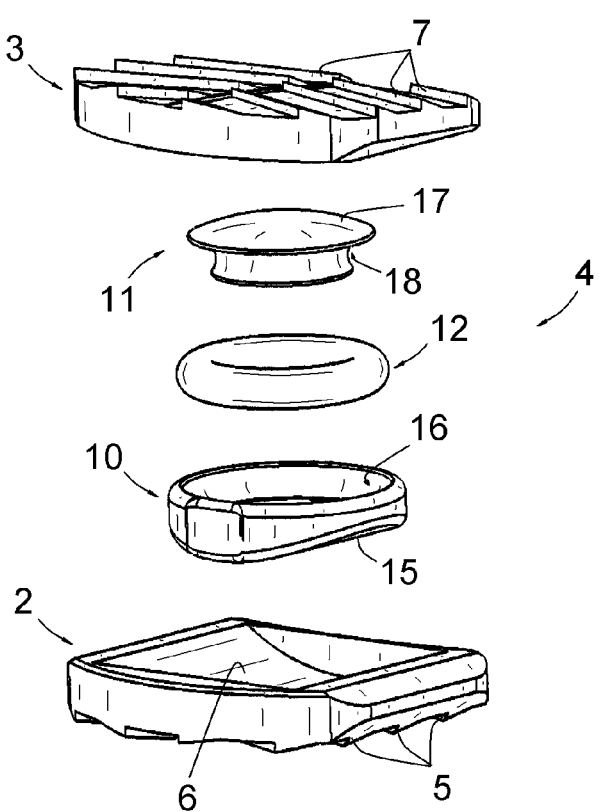
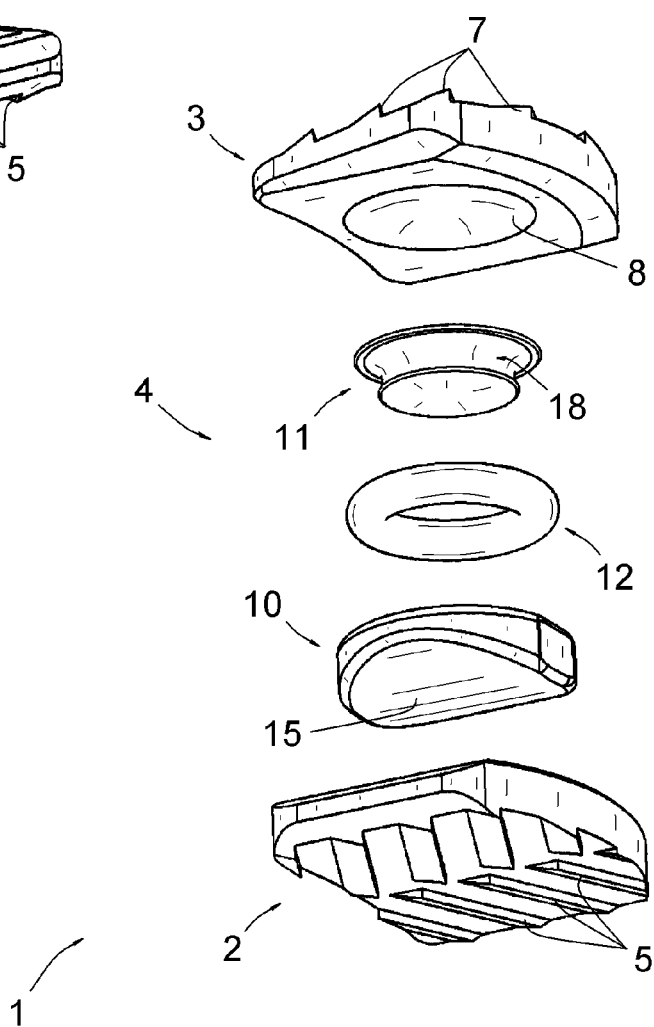
FIG. 1
FIG. 2

INTERVERTEBRAL DISK PROSTHESIS NOTABLY FOR CERVICAL VERTEBRAE

The present invention relates to an intervertebral disk prosthesis, notably for cervical vertebrae.

It is known how to make intervertebral disk prostheses in two or three elements. When the prosthesis comprises two elements, these elements have mating articular surfaces allowing direct jointing of one element with the other. When the prosthesis comprises three elements, the two elements anchored to the respective vertebrae are each jointed with an intermediate sliding element, forming two articular surfaces for cooperation with these elements.

The existing intervertebral disk prostheses, particularly those intended for cervical vertebrae, do not give perfect satisfaction. Indeed, these prostheses do not always perfectly reproduce the natural movements of vertebrae. Further, the repeated movements to which they are subject, result in more or less rapid wear of the articular surfaces, which, in the case of cervical disk prostheses, have reduced dimensions. This wear leads to alteration of the articular movement and to an undesirable diffusion of particles into the organism of the patient.

When the prosthesis comprises three elements, there is moreover a notable risk of expulsion of the intermediate element.

Documents US 2004/054411, EP 1 532 950, WO 2005/079407 or US 2005/165485 describe various prostheses of the prior art, with which no remedy may be found for these drawbacks.

The main object of the present invention is to provide an intervertebral disk prosthesis, notably for cervical vertebrae, finding a remedy to the drawbacks of the prostheses of the prior art, and in particular allowing the natural movements of the vertebrae to be perfectly reproduced.

Another object of the invention is to provide a prosthesis in which the wear of the articular surfaces remains reduced.

Another further object of the invention is to provide a prosthesis having a reduced risk of expulsion of an intermediate element.

An additional object of the invention is to provide a prosthesis remaining relatively simple to assemble.

The relevant prosthesis in a way known per se comprises at least two elements intended to be jointed relatively to each other, at least two of which are flattened and intended to be connected to the respective vertebral plates of two vertebrae.

According to the invention, at least one of the elements of the prosthesis comprises two elements independent of each other, i.e. a first portion and a second portion, at least one of which includes an articular surface, said first portion and said second portion each comprising a circular seat delimited by an arched wall;

said element comprises an O-ring in an elastically deformable material;

one of said seats is dimensioned in order to receive a radially outer portion of this ring while the other seat is dimensioned in order to receive a radially inner portion of this ring.

The prosthesis according to the invention thus comprises an O-ring in an elastically deformable material, interposed between a first portion and a second portion of an element, which allows a damped movement of this second portion relatively to this first portion, and therefore globally a damped movement of a flattened element relatively to the other flattened element. This damping occurs both during a movement with a main component oriented along a direction substantially perpendicular to the plane in which a flattened element extends, and during a movement having a main component directed along a direction substantially parallel to this same plane. The first movement is therefore the one in which a "compressional force" is exerted after implantation, along the longitudinal axis of the vertebral column, a on the vertebrae, the second movement is the one which is exerted, after implantation, substantially perpendicularly to the longitudinal axis of the vertebral column, along a direction which may be anteroposterior or transverse, or combining an anteroposterior and transverse displacement.

This dual possibility of a damped movement proves to be better able to reproduce the natural movements of the vertebrae and to substantially reduce the wear of the articular surfaces of the prosthesis.

The circular shape of the seats provides to the ring a wide support against said first portion and said second portion, preventing wear or deterioration of this ring, notwithstanding the repeated movements which the prosthesis undergoes.

The prosthesis according to the invention may be of the aforementioned type in two flattened elements, one of which comprises both independent portions. Said first portion forms said flattened element and the second portion includes said articular surface.

The prosthesis may also be of the aforementioned type comprising three elements; said element in two portions is then preferably the intermediate element, said first portion comprising one of the articular surfaces which this intermediate comprises, and said second portion including the other articular surface which this intermediate element comprises.

The prosthesis according to the invention, when it is in three elements, proves to be able to reduce to a certain extent the risk of expulsion of the intermediate element by means of the aforementioned dual possibility of a damped movement.

Preferably, each of said arched walls extends, as seen in a cross-section, over an arc corresponding to an angle of more of 90 degrees, so that the ring has to be elastically deformed in order to be able to be inserted into the seat delimited by this wall, and therefore this wall is retentive of the ring.

Both seats are thus retentive, and the ring is "snapped on" in both of these seats in order to achieve the assembling of said second portion to said first portion. Assembling the prosthesis is, in this way, achieved in a simple and easy way.

According to a simple embodiment of the invention, the seat receiving the radially outer portion of the ring is laid out in said first portion while the seat receiving the radially inner portion of the ring is laid out in said second portion.

Said second portion is thus circumscribed by said first portion.

According to another aspect of the invention, when the prosthesis comprises three elements as aforementioned, i.e. two flattened elements and an intermediate element, the flattened element intended to be connected to the overlying vertebra comprises a spherical and concave articular surface, and the intermediate element comprises a conjugate spherical and convex articular surface, and the flattened element intended to be connected to the underlying vertebra comprises a cylindrical and concave articular surface, the generatrix of which is directed after implantation in the anteroposterior direction and the intermediate element comprises a conjugate cylindrical and convex articular surface.

This structure proves to be able to reproduce the natural movement of the vertebrae under the best conditions, in particular in combination with the aforementioned possibility of a damped movement.

Preferably, in this case, the radius generating the spherical articular surfaces of the flattened element intended to be connected to the overlying vertebra and of the intermediate element is such that the centre of rotation allowed by these surfaces is located after implantation below the vertebral plate of the underlying vertebra, and the radius generating the cylindrical articular surfaces of the flattened element intended to be connected to the underlying vertebra and of the intermediate element is such that the centre of rotation allowed by these surfaces is located after implantation above the vertebral plate of the overlying vertebra.

The thereby conformed prosthesis reproduces the anatomic movement under the best conditions;

Preferably, said cylindrical and concave articular surface has a dimension, in the anteroposterior direction larger than the dimension in the anteroposterior direction of said conjugate articular surface of the intermediate element, so that this intermediate element is mobile in the anteroposterior direction relatively to the flattened element intended to be connected to the underlying vertebra.

This mobility is also favorable for reproducing the anatomic movement under the best conditions.

Said cylindrical and concave articular surface and said conjugate articular surface may be congruent, said spherical articular surfaces may be congruent and these different articular surfaces may have identical radii of curvature.

Said cylindrical and concave articular surface and said conjugate articular surface may be congruent, said spherical articular surfaces may be congruent and the radius of curvature of said cylindrical and concave articular surface and of said conjugate articular surface may be different from the radius of curvature of said spherical articular surfaces.

The invention will be better understood, and other features and advantages of the latter will become apparent with reference to the appended schematic drawing, illustrating as non-limiting examples, several possible embodiments of the prosthesis to which it relates.

FIG. 1 is a perspective view thereof before assembly, according to one embodiment;

FIG. 2 is a view thereof similar to FIG. 1, according to another viewing angle;

FIGS. 1-8 illustrate an intervertebral disk prosthesis 1 notably for cervical vertebrae, comprising two flattened elements 2, 3 intended to be anchored to the respective vertebrae, and an intermediate element 4 on which the elements 2, 3 are intended to be jointed.

Figure 9:
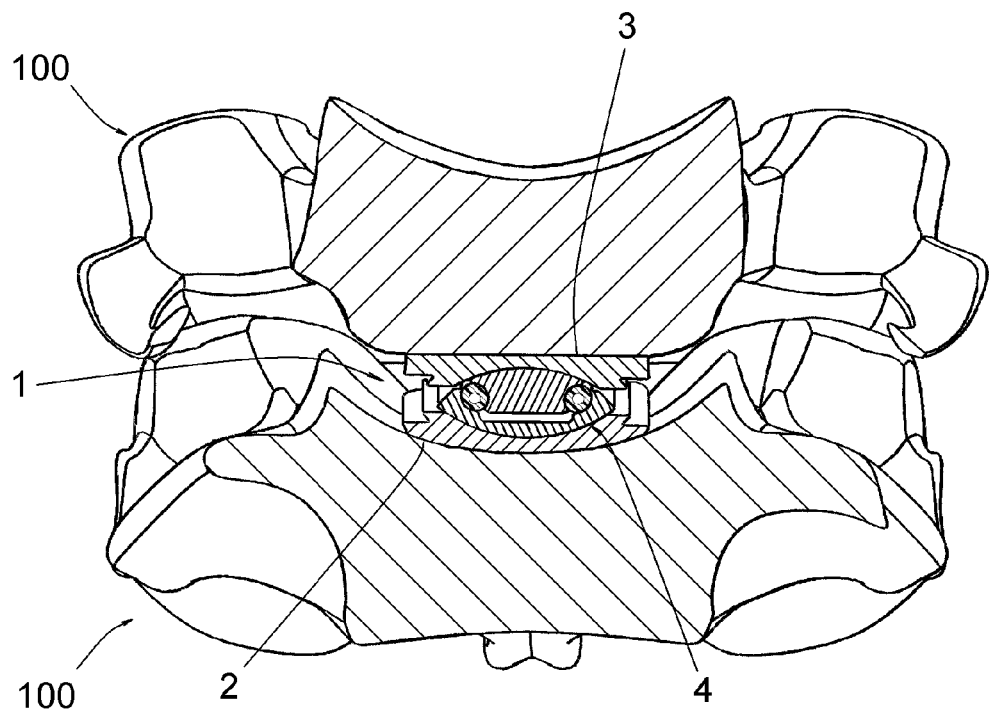
FIGS. 9 and 10 are views thereof after implantation on vertebrae, as a vertical sectional view, in the frontal plane and in the sagittal plane respectively.
Figure 10:
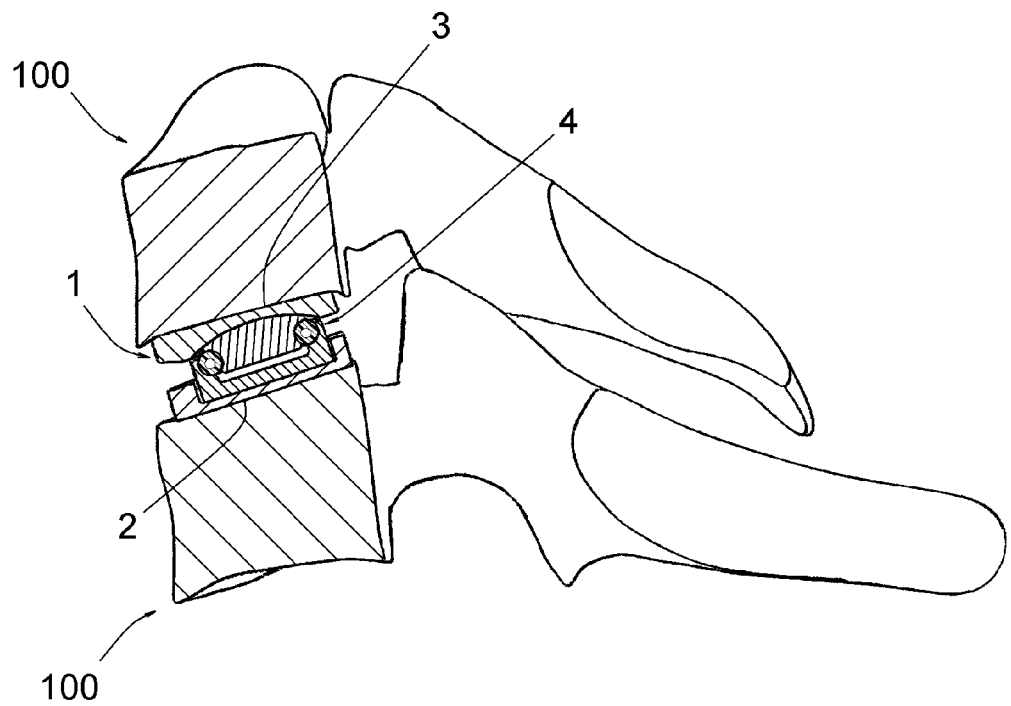

As this appears in FIGS. 9 and 10, the element 2 is intended to be connected to the underlying vertebra 100 and for this purpose comprises on its face intended to bear against the plate of this vertebra, reliefs 5 promoting adhesion of this element 2 to this plate. On its opposite face, the element 2 comprises an articular cavity delimited by a cylindrical and concave surface 6, the generatrix of which is directed after implantation in the anteroposterior direction. The radius of generation of this surface 6 has a length from 6 to 15 mm for a cervical disk prosthesis, so that the centre of generation of this surface is found clearly above the element 3, being located after implantation above the vertebral plate of the overlying vertebra.

Said articular cavity has a dimension, in the anteroposterior direction, larger than the dimension in the anteroposterior direction of said conjugate articular surface 15 described later on, of the intermediate element 4, so that this intermediate element 4 is mobile in the anteroposterior direction relatively to the element 2.

The element 3 is intended to be connected to the overlying vertebra and comprises in the same way on its face intended to come against the plate of this vertebra, reliefs 7 promoting adhesion of this element 3 to this plate. On its opposite face, the element 3 comprises an articular cavity delimited by a spherical and concave surface 8. The radius generation of this surface has a length from 6 to 15 mm for a cervical disk prosthesis, so that the centre of generation of this surface is clearly found below the element 2, being located after implantation below the vertebral plate of the underlying vertebra.

The intermediate element 4 comprises two portions 10, 11 independent of each other, i.e. a first portion 10 and a second portion 11 and an O-ring 12 in an elastically deformable material.

The portions 10 and 11, like the element 2 and 3, are notably made in a biocompatible stiff material such as in ceramic and the ring 12 is in a biocompatible elastic material such as in biocompatible silicone.

Figure 3:
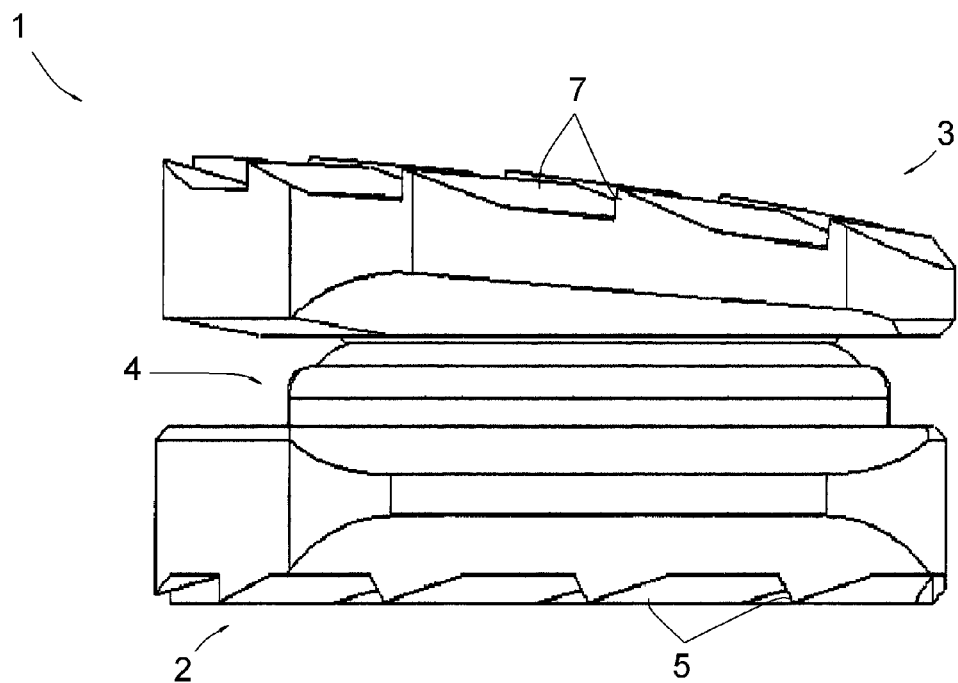
FIG. 3 is a side view thereof.
Figure 4:
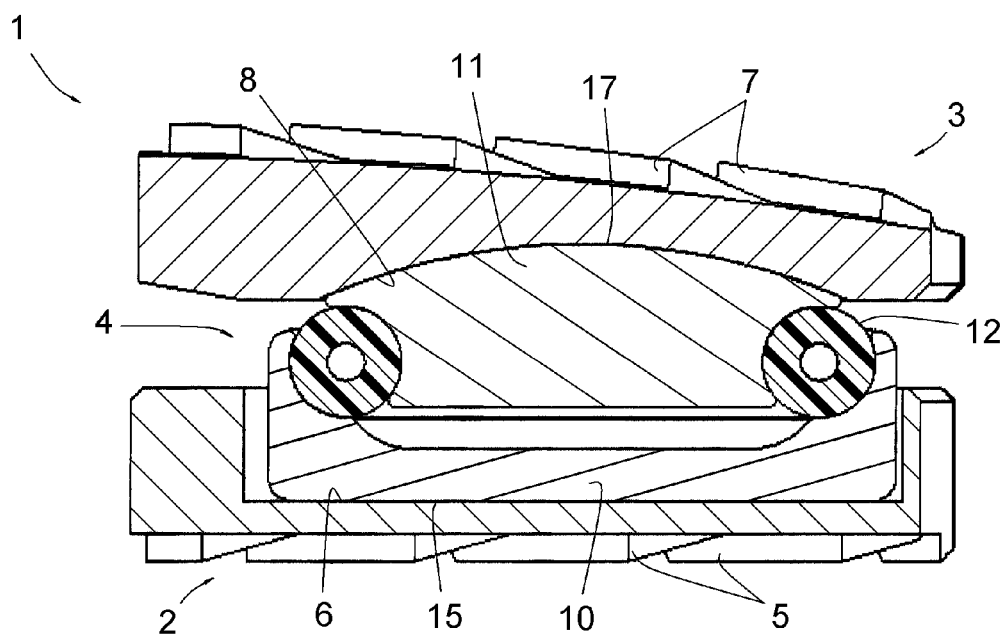
FIG. 4 is a view thereof similar to FIG. 3, as a sectional view along a median anteroposterior plane.
Figure 5:
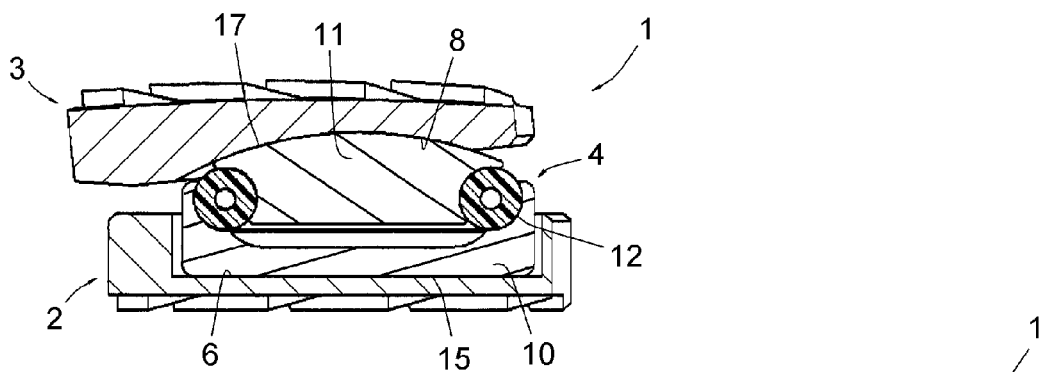
FIG. 5 is a view thereof similar to FIG. 4, in a position of the elements making up the prosthesis corresponding to flexure of the vertebral column.
Figure 6:
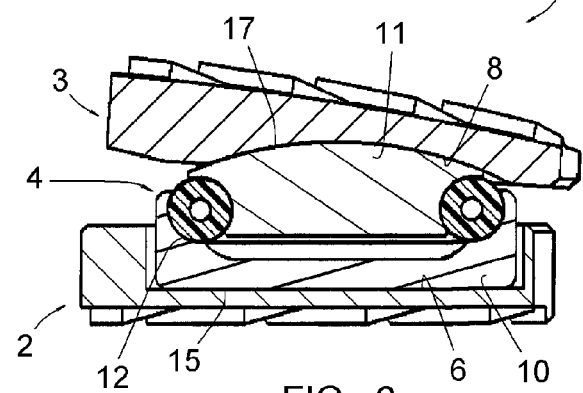
FIG. 6 is a view thereof similar to FIG. 4, in a position of the elements making up the prosthesis corresponding to an extension of the vertebral column.
Figure 7:
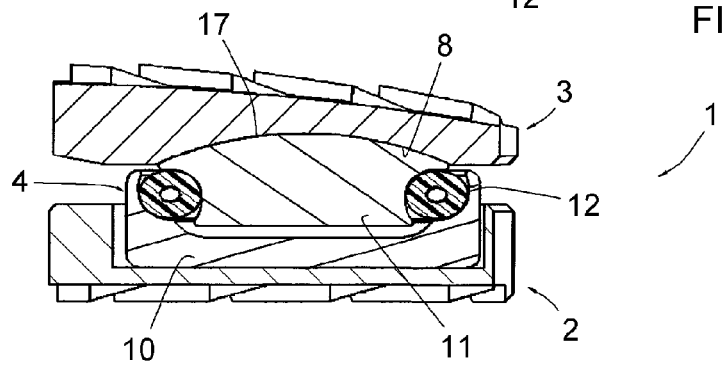
FIG. 7 is a view thereof similar to FIG. 4, in a position of the elements making up the prosthesis corresponding to a compressional movement of the vertebral column, i.e. along the axis of this vertebral column.
Figure 8:
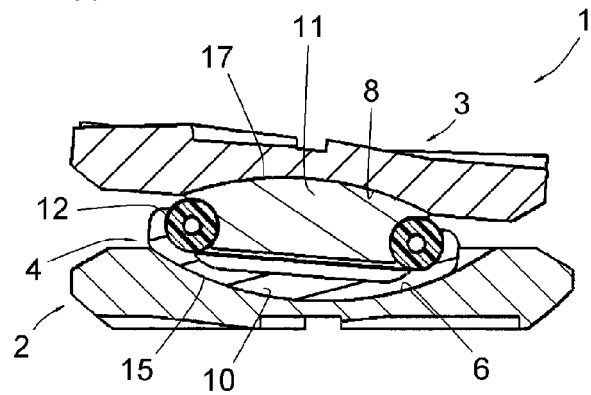
FIG. 8 is a sectional view thereof along a median transverse plane in a position of the elements making up the prosthesis corresponding to lateral inflection of the vertebral column.

As this is more particularly visible in FIGS. 4 and 8, the first portion 10 comprises a bottom and a peripheral wall. This bottom forms a cylindrical and convex lower surface 15 congruent with the surface 6. The peripheral wall comprises on its internal face, a circular recess 16 delimited by an arched wall, forming a dimensioned seat for receiving a radially outer portion of the ring 12. It is shown in FIG. 4 that this arched wall extends, as seen cross-sectionally, over an arc corresponding to an angle of the order of 110 degrees.

The second portion 11 is circular and comprises a congruent spherical and convex upper face 17 of the surface 8, and a circular peripheral recess 18. This recess 18 is delimited by an arched wall, forming a dimensioned seat for receiving a radially inner portion of the ring 12. It is shown on FIG. 4 that this arched wall extends, as seen cross-sectionally, over an arc corresponding to an angle of 110 degrees.

The ring 12 should thus be slightly elastically deformed so as to be able to be inserted into the seats formed by the recesses 16 and 18, said arched wall being thus retentive of this ring. With the latter, assembling said second portion 11 to the first portion 10 may thereby be performed and therefore the element 4 may be made up in a simple and rapid way.

As shown in FIGS. 5-8, the spherical faces 8 and 17 allow an articular movement of the element 3 relatively to the element 4 in the anteroposterior direction (cf. FIGS. 5 and 6) and an articular movement in the transverse direction (cf. FIG. 8); the cylindrical faces 6 and 15 allow an articular movement of the element 4 relatively to the element 12 in the transverse direction (cf. FIG. 8). These different movements combine depending on the movements of the vertebrae, and the thereby conformed prosthesis 1 proves to be able to reproduce the natural movement of the vertebrae under the best conditions. This prosthesis 1 further allows a notable reduction in the risk of expulsion of the intermediate element 4 by the dual possibility of damped movement made possible by the O-ring 12, i.e. during a movement having a main component oriented along a direction substantially perpendicular to the plane in which a flattened element 2, 3 extends (axial compression of the ring 12, cf. FIG. 7), and during a movement having a main component directed along a direction substantially parallel to the same plane (radial compression of the ring 12). The first movement is therefore the one which is exerted after implantation along the longitudinal axis of the vertebral column; the second movement is the one which is exerted after implantation substantially perpendicularly to the longitudinal axis of the vertebral column, along a direction which may be anteroposterior or transverse or combining an anteroposterior and transverse displacement.

During these axial and radial compressions of the ring 12, the circular shape of the seats formed by the recesses 16 and 18 provides this ring with a large support against said second portion 11 and said first portion 10, preventing wear or deterioration of this ring.

Figure 11:
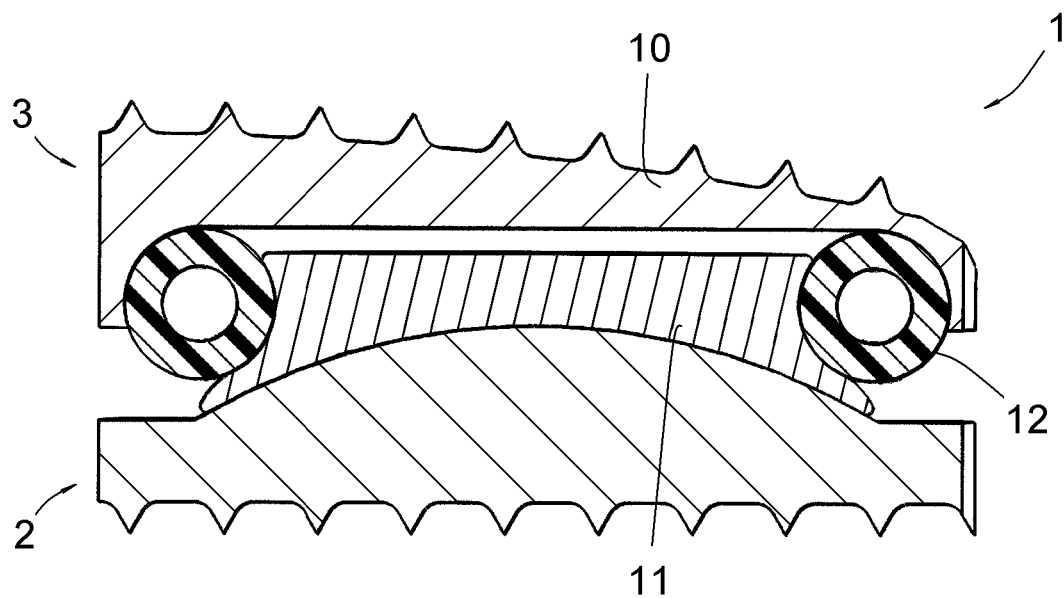
FIG. 11 is a view of the prosthesis according to another embodiment as a vertical sectional view.
Figure 12:
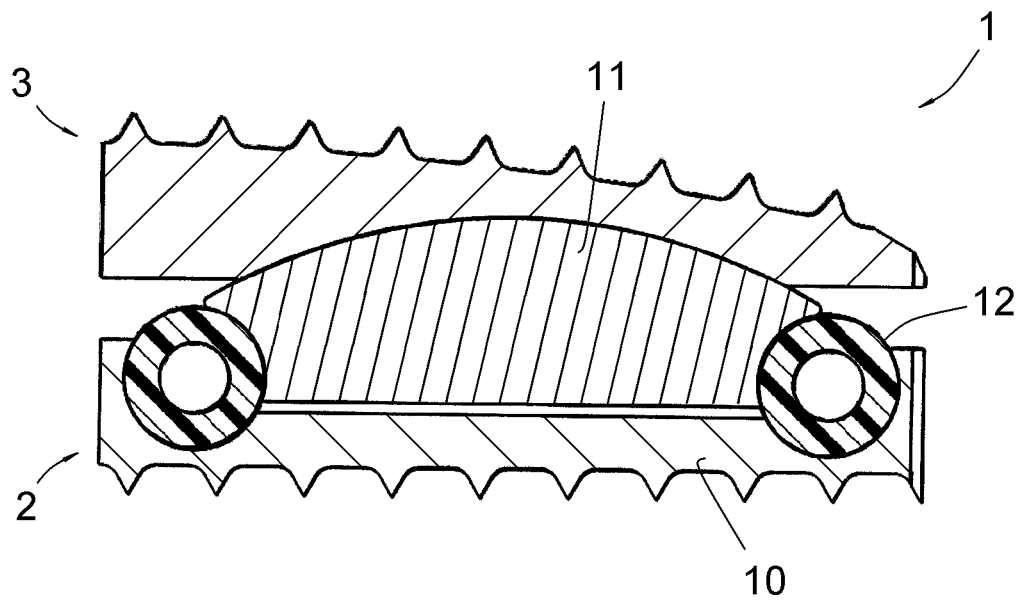
FIG. 12 is a view of the prosthesis according to still another embodiment, also as a vertebral sectional view.

The prosthesis 1 described above is a prosthesis comprising three element, i.e. with interposition of an intermediate element 4 between the flattened elements 2 and 3 attached to the vertebrae. FIGS. 11 and 12 show two exemplary applications of the invention on prostheses in two flattened elements 2, 3, i.e. with jointing of the elements 2 and 3 directly with each other.

In the exemplary embodiment shown in FIG. 11, the upper element 3 is in two portions 10, 11 with the ring 12 between the latter; in the exemplary embodiment shown in FIG. 12, it is the lower element 2 which is in two portions 10, 11.

As this is apparent from the foregoing, the invention provides a intervertebral disk prosthesis, notably for cervical vertebrae, having determining advantages relatively to the homologous prostheses of the prior art, in particular those of having reduced wear of the articular surfaces, of having a reduced risk of expulsion of the intermediate element, when it comprises such an element, and of remaining relatively simple and rapid to assemble.

The invention was described above with reference to an embodiment given as a pure example. It is obvious that it is not limited to this embodiment but that it extends to all embodiments covered by the appended claims herein. Thus, the prosthesis may not comprise any intermediate element, in which case at least one of its flattened elements would comprise two portions independent of each other, i.e. a first portion intended to be connected to the plate of the vertebra and a second portion including the articular surface comprised by this element, said ring being placed between this first portion and this second portion.

The invention claimed is:

1. An intervertebral disk prosthesis notably for cervical vertebrae, comprising:
   two flattened elements, each of the two flattened elements having a main surface extending in a first plane;
   a first flattened element of the two flattened elements forms a first circular seat extending in a plane parallel to said first plane, delineated by a first, radially inward oriented, concave wall, the first concave wall being arched-shaped when viewed in a second plane perpendicular to said first plane;
   a second flattened element of the two flattened elements forms a second circular seat extending in the plane parallel to said first plane, delineated by a second, radially outward oriented, concave wall, the second concave wall being arched-shaped when viewed in said second plane;
   an O-ring element comprising an elastically deformable and compressible material, the O-ring element capable of being elastically deformed and compressed radially and axially; and
   a diameter of said first circular seat being such that said first circular seat receives a radially outer portion of the O-ring element and a diameter of said second circular seat being such that said second circular seat receives a radially inner portion of the O-ring element.

2. The intervertebral disk prosthesis according to claim 1, wherein
   the intervertebral disk prosthesis includes two plate-like elements anchored on vertebral plates of respective adjacent vertebrae, each plate-like element forming an articular surface;
   one of said two flattened elements is a first intermediate element including an articular surface adapted to cooperate with the articular surface of a first plate-like element of the two plate-like elements; and
   the other of said two flattened elements is a second intermediate element including an articular surface adapted to cooperate with the articular surface of a second plate-like element of the two plate-like elements.

3. The intervertebral disk prosthesis according to claim 2, wherein
   one plate-like element of the two plate-like elements is configured to be connected to an overlying vertebra and the articular surface of the one plate-like element is spherical and concave and the articular surface of the first intermediate element is spherical and convex, and
   the other plate-like element of the two plate-like elements is configured to be connected to the underlying vertebra and the articular surface of the other plate-like element includes a cylindrical and concave articular surface, a generatrix of the cylindrical and concave articular surface being directed after implantation in an anteroposterior direction relative to the vertebra, and the articular surface of the second intermediate element is cylindrical and convex.

4. The intervertebral disk prosthesis according to claim 3, wherein said cylindrical and concave articular surface of the plate-like element has a dimension in the anteroposterior direction larger than a dimension in the anteroposterior direction of said cylindrical and convex conjugate articular surface of the second intermediate element, so that the second intermediate element is mobile in the anteroposterior direction relative to the other flattened element configured to be connected to the underlying vertebra.

5. The intervertebral disk prosthesis according to claim 3, wherein
   said cylindrical and concave articular surface of the plate-like element and said cylindrical and convex conjugate articular surface of the second intermediate element are congruent,
   said spherical articular surfaces are congruent, and
   the different articular surfaces have identical radii of curvature, respectively.

6. The intervertebral disk prosthesis according to claim 3, wherein
said cylindrical and concave articular surface of the plate-like element and said cylindrical and convex conjugate articular surface of the second intermediate element are are congruent,
said spherical articular surfaces are congruent, and
a radius of curvature of said cylindrical and concave articular surface of the plate-like element and a radius of said cylindrical and convex conjugate articular surface of the second intermediate element are is different from a radius of curvature of said spherical articular surfaces.

7. The intervertebral disk prosthesis according to claim 3, wherein
a radius of (i) the spherical articular surfaces of the one plate-like element configured to be connected to the overlying vertebra and of (ii) the first intermediate element is such that a center of rotation is located after implantation below the vertebral plate of the underlying vertebra, and
a radius of (i) the cylindrical articular surfaces of the other plate-like element configured to be connected to the underlying vertebra and of (ii) the second intermediate element is such that a center of rotation is located, after implantation, above the vertebral plate of the overlying vertebra.

8. The intervertebral disk prosthesis according to claim 1, wherein
one of said two flattened elements is a first plate-like element anchored on a vertebral plate of a first vertebra,
the intervertebral disk prosthesis includes a second plate-like element anchored on the vertebral plate of a second vertebra adjacent the said first vertebra and having an articular surface, and
the other flattened element of the two flattened elements is an intermediate element including an articular surface adapted to cooperate with the articular surface of said second plate-like element.

9. The intervertebral disk prosthesis according to claim 8, wherein
said first plate-like element is configured to be connected to an overlying vertebra,
said second plate-like element is configured to be connected to an underlying vertebra and includes a spherical and convex articular surface, and
said articular surface of said intermediate element is a spherical and concave articular surface.

10. The intervertebral disk prosthesis according to claim 8, wherein
said first plate-like element is configured to be connected to an underlying vertebra,
said second plate-like element is configured to be connected to an overlying vertebra and includes a spherical and concave articular surface, and
said articular surface of said intermediate element is a spherical and convex articular surface.

11. The prosthesis according to claim 1, wherein
each of said concave walls extends, when viewed in said second plane, over an arc greater than 90 degrees, so that the O-ring element is elastically deformed and compressed when inserted into the respective circular seat delimited by the concave wall, the concave wall retains the O-ring.

12. The prosthesis according to claim 1, wherein said O-ring comprises a center and a radially inner circular edge and a radially outer circular edge, said radially inner circular edge being closer to said center than said radially outer circular edge.

* * * * *